(12) United States Patent
Townsend

(10) Patent No.: US 7,560,246 B2
(45) Date of Patent: *Jul. 14, 2009

(54) COMPOSITIONS AND METHODS FOR DETECTING TARGET MICROORGANISMS IN A SAMPLE

(75) Inventor: David E Townsend, Sammamish, WA (US)

(73) Assignee: BioControl Systems, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/940,682

(22) Filed: Aug. 27, 2001

(65) Prior Publication Data

US 2002/0058298 A1 May 16, 2002

Related U.S. Application Data

(63) Continuation-in-part of application No. 08/484,593, filed on Jun. 7, 1995, now Pat. No. 6,387,650.

(60) Provisional application No. 60/228,956, filed on Aug. 28, 2000.

(51) Int. Cl.
*C12Q 1/04* (2006.01)
(52) U.S. Cl. .............................. 435/34; 435/4; 435/243
(58) Field of Classification Search .................. 435/29, 435/32, 34, 36, 7.72, 24; 424/94.6, 94.63
See application file for complete search history.

(56) References Cited

U.S. PATENT DOCUMENTS

| | | | | |
|---|---|---|---|---|
| 4,140,580 A | | 2/1979 | Gibson et al. ................ | 195/100 |
| 4,591,554 A | | 5/1986 | Koumura et al. ............... | 435/18 |
| 4,925,789 A | | 5/1990 | Edberg ......................... | 435/38 |
| 5,064,756 A | * | 11/1991 | Carr et al. ....................... | 435/32 |
| 5,330,889 A | * | 7/1994 | Monget ......................... | 435/34 |
| 5,420,017 A | * | 5/1995 | Tuompo et al. ................ | 435/29 |
| 5,700,655 A | | 12/1997 | Croteau et al. ................. | 435/30 |
| 5,849,515 A | * | 12/1998 | Grant | |
| 5,891,709 A | * | 4/1999 | Stern et al. | |
| 6,287,797 B1 | | 9/2001 | Croteau et al. ................ | 435/30 |
| 6,368,847 B1 | * | 4/2002 | Line et al. | |

FOREIGN PATENT DOCUMENTS

WO     WO 96/40980     12/1996

OTHER PUBLICATIONS

Manafi et al, Journal of Applied Bacteriology, 1990, vol. 69, No. 6, pp. 822-827.*
Molina et al, "Utilidad de la prueba de la L-alanina-aminopeptidasa para diferencian la estructura de la pared celular de las bacterias" Enfermedades Infecciosas Y Microbiologia Clinica, 1991, vol. 9, Issue 10, pp. 637-639. [Spanish Language, abstract in English].*
Clark et al, "Simple Color Tests Based on an Alanyl Peptidase Reaction Which Differentiate *Listeria monocytogenes* from Other *Listeria* Species", Journal of Clinical Microbiology, Aug. 1997, vol. 35, No. 8, pp. 2155-2156.*
Bennett et al, "Use of pyrrolidonyl peptidase to distinguish *Citrobacter* from *Salmonella*" Letters in Applied Microbiology, 1999, vol. 28, pp. 175-178.*
Corry et al., "Culture media for the isolation of *campylobacters*," *International Journal of Food Microbiology* 26: 43-76, 1995.
De Man, J.C., "The Probability of Most Probable Numbers," *European J. Appl. Microbiol.* 1: 67-78, 1975.
Stern and Line, "Comparison of Three Methods for Recovery of *Campylobacter* spp. From Broiler Carcasses," *Journal of Food Protection* 55(9): 663-666, Sep. 1992.
Stern et al., "A Differential-selective Medium and Dry Ice-generated Atmosphere for Recovery of *Campylobacter jejuni*," *Journal of Food Protection* 55(7): 514-517, Jul. 1992.
Thomas, Jr., H.A., "Bacterial Densities From Fermentation Tube Tests," *J. Am. Water Works Assoc.* 34(4): 572-576, 1942.

* cited by examiner

*Primary Examiner*—L Blaine Lankford
*Assistant Examiner*—Allison M. Ford
(74) *Attorney, Agent, or Firm*—Seed IP Law Group PLLC

(57) ABSTRACT

The present invention relates generally to compositions and methods for detecting target microorganisms in a sample. In particular, the present invention relates to compositions comprising a conditionally detectable maker and an enzyme substrate that provides detection of the target microorganism as well as methods of use thereof. With the invention disclosed herein, a widely applicable approach is revealed which utilizes a presumptive indicator for the target microorganism and non-target microorganisms capable of growth and detection in a medium followed by a confirmation indicator, which is substantially only reacted upon by the non-target microorganisms.

6 Claims, 1 Drawing Sheet

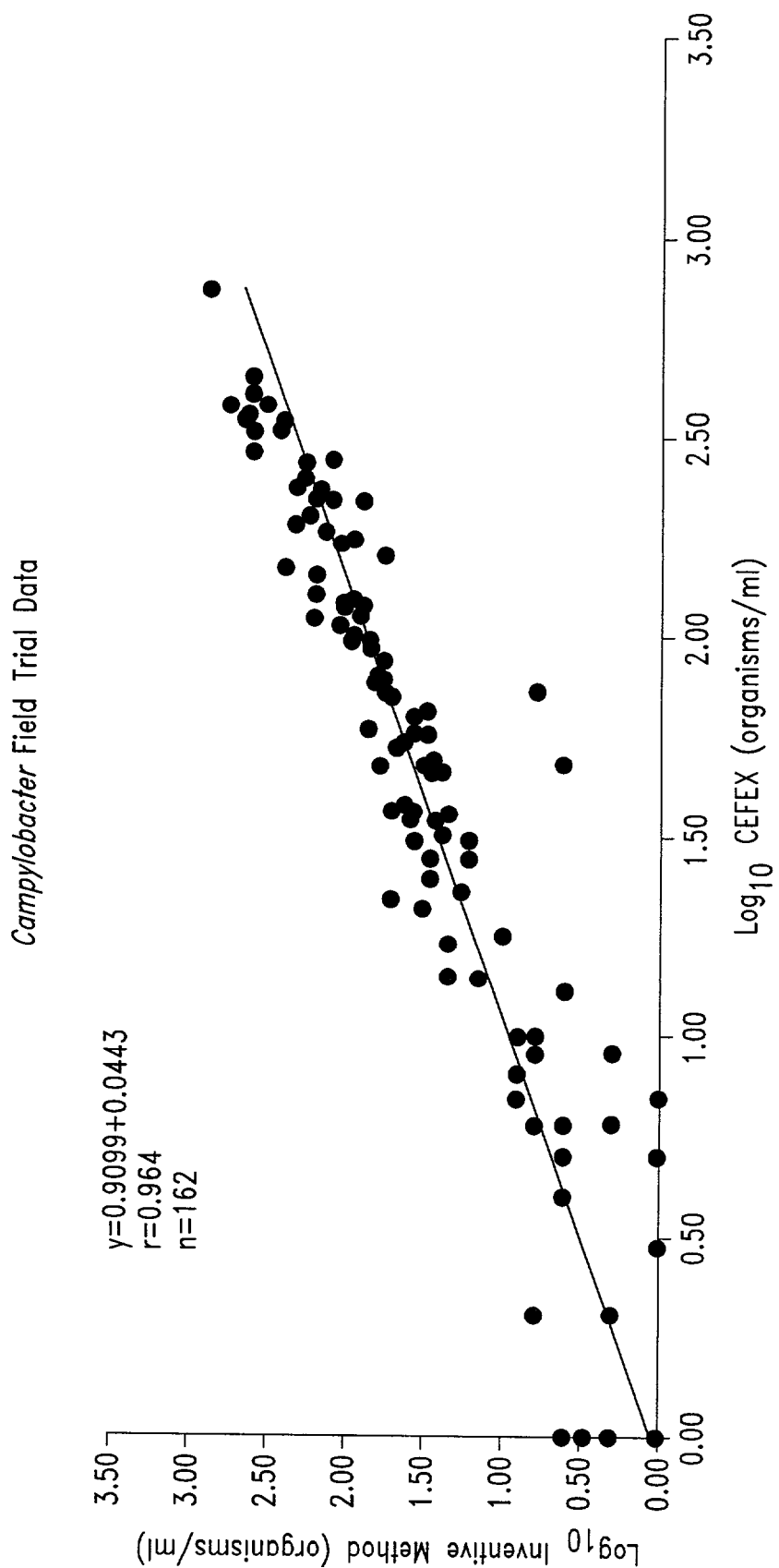

US 7,560,246 B2

COMPOSITIONS AND METHODS FOR DETECTING TARGET MICROORGANISMS IN A SAMPLE

CROSS REFERENCE TO RELATED APPLICATION

The present application claims priority to U.S. Provisional Application No. 60/228,956, filed Aug. 28, 2000 and is a continuation-in-part of U.S. patent application Ser. No. 08/484,593, filed Jun. 7, 1995, issued as U.S. Pat. No. 6,387,650.

TECHNICAL FIELD

The present invention relates generally to compositions and methods for detecting target microorganisms in a sample. In particular, the present invention relates to compositions comprising a conditionally detectable maker and an enzyme substrate that provides detection of the target microorganism as well as methods of use thereof.

BACKGROUND OF THE INVENTION

The development of a diagnostic test for the detection of a specific type of microorganism in a test sample is a very slow and difficult process due to several factors. First, to develop a diagnostic test for a specific microorganism one must identify a way to detect it in a manner which is highly sensitive and easily recognizable. Generally, this is accomplished by incorporating a detection molecule into the growth medium that interacts with the target microorganism biochemically to produce a measurable signal. The best type of signals are those which result in a color change of the growth medium. Second, the signal should not interact with the matrix of the test sample resulting in a false positive reaction. This is particularly problematic if the test sample is derived from a living or once living entity such as a food product because such entities possess many of the same biochemical processes of a target microorganism. Finally, most test agents, for example a raw food product, can be contaminated by literally billions of microorganisms of differing types per gram of food. As a result, a useful diagnostic test should possess a high selectivity for the target microorganism. This is generally accomplished by either incorporating a "cocktail" of antimicrobial agents into the growth medium to suppress the growth and detection of non-target microorganisms or by selecting a detection molecule that is not recognized by a vast majority of non-target microorganisms.

Microbial growth indicators normally react chemically with a metabolic by-product produced by target microbes resulting in a color change in the medium. Examples of chemicals which changes color in the presence of pH changes associated with microbial growth include aniline blue, phenol red, bromocresol blue, and neutral red. For example, Gibson, U.S. Pat. No. 4,140,580 uses aniline blue, a chemical which changes color in the presence of acidic metabolic waste products produced by yeasts.

Enzymatic catalysis for hydrolyzing chromogenic or fluorogenic substrates to yield a detectable signal has been used in a number of microbial diagnostic applications.

One example of this detection methodology utilizes testing for the presence of various enzymes of the targeted microorganism(s). For example, Townsend and Chen, describes a method and composition for detecting bacterial contamination in food products in U.S. application Ser. No. 08/484,593, filed Jun. 7, 1995, which is incorporated by reference herein. This growth medium detects bacterial contamination in a sample by detecting bacterial enzymes (e.g., phosphatase, βglucosidase, and L-alanine-aminopeptidase) from diverse microbial species. The liberated fluorescent moieties exhibit detectable signals with an identical emission wavelength. This procedure takes advantage of combining different bacterial enzyme activities from diverse microbes to create a broader enzyme activity spectrum; the broadened spectrum enables the detection of total bacteria in a test sample.

Koumura et. al., in U.S. Pat. No. 4,591,554 describe the use of 4-methylubelliferyl derivatives fluorogenic analysis to detect and determine the number of microorganisms based on the amount of liberated umbelliferone derivatives. According to the method, microorganisms at more than 10,000 cfu/ml can be determined by contacting a sample solution with the umbelliferone derivatives, and measuring the amount of fluorescent umbelliferone derivatives liberated. In the Koumura patent, cell lysis is required to increase the amount of liberated enzymes. In other cases, pH adjustment of the mixture and centrifugation of the mixture to remove insoluble cells are required at the end of incubation.

Edberg et. al. in U.S. Pat. No. 4,925,789 describe the use of enzyme substrates as nutrient indicators containing a nutrient moiety covalently linked to a non-metabolized detectable moiety that are specifically hydrolyzed by targeted microorganisms. In the Edberg patent, the nutrient indicators are specifically selected to be hydrolyzed by only the targeted microorganisms by virtue of their presence in the growth medium as a primary nutrient source. Non-target microorganisms are not detected in this system and are suppressed by the addition of antimicrobial agents.

While the aforementioned strategies are useful they are not particularly suited to all types of detection, especially when antimicrobial agents wish to be avoided for enhanced sensitivity. For example, most antimicrobial agents are designed to be effective against a wide spectrum of microorganisms. As a result, the use of these agents in a diagnostic test can often negatively impact the growth and detection of the target microorganism resulting in lowered sensitivity for the test. Furthermore, very few cocktails of antimicrobials are effective at suppressing all non-target growth resulting in lowered specificity for the test. In addition, while the use of a highly selective detection molecule may overcome these obstacles, such detection molecules are rare.

As it may be useful to detect any number of specific microorganisms, the prototypical example set forth for discussion purposes only is the bacterial species *Campylobacter*. *Campylobacter* species are gram-negative, oxidase-positive, curved or spiral rod-shaped bacteria. *Campylobacter* are a major cause of food poisoning, primarily from poultry products, and their incidence in outbreaks of gastrointestinal disease appears to be on the rise. The United States Department of Agriculture is leading the effort to reduce the levels of *Campylobacter* contamination on poultry products by developing methods for the detection and quantification of *Campylobacter* in poultry rinse water samples. In the most widely used current procedure (United States Department of Agriculture ARS, Poultry Microbiological Safety Research Unit, Method for the Enumeration of *Campylobacter* species from Poultry Rinses, Mar. 15, 2000; Also see, Stem et al., *J. Food Prot.* 55:663-666, 1992 and Stem et al., *J. Food Prot.* 55:514-517, 1992, incorporated by reference in their entirety)) 400 ml of buffered phosphate water (BPW) is added to a strong plastic bag containing a raw chicken carcass. The bag is twisted, and the contents shaken for 2 minutes to liberate any *Campylobacter* from the surface of the chicken into the BPW. After rinsing, at least 40 ml of rinse water is transferred to a sterile container and held on ice until it can be tested for the presence of *Campylobacter*. To quantify the *Campylobacter*, 0.25 ml aliquots of rinse water are spread onto four plates of agar based medium (either Campy-Line agar or Campy CEFEX agar, recipe available from United States Department of Agriculture ARS, Poultry Microbiological Safety Research Unit; also available from Hardy Diagnostics, Santa Maria, Calif.). Next, 0.1 ml aliquots of rinse water are spread onto two additional plates of medium. These six plates are then placed in a 42° C. microaerophillic incubator and incubated for 48 hours. Resulting colonies that resemble typical *Campylobacter* species are observed microscopically to visualize cell shape and the presence of cell motility. Typical comma-shaped cells are finally subjected to a slide agglutination test to confirm the presence of *Campylobacter*.

This method, although widely accepted, has a number of disadvantages the most important of which is that the method requires a large number of complicated steps to confirm that the organisms growing on the plates are in-fact *Campylobacter*. As with most microorganism detection assays, these steps are very expensive to run, require the skills of a highly trained microbiologist to perform, and significantly limit the number of tests that can be performed in a normal laboratory shift. As a result, short cuts are made by the technicians performing the tests to complete their work on-time which can result in highly erroneous data, thus, affecting the quality of the food being prepared. Therefore, there is a need for improved tests for the detection of *Campylobacter*. If the confirmation step could be simplified, and test results obtained in a shorter more cost effective manner, it would allow manufacturers to release product with more accurate information regarding the true *Campylobacter* concentration. Obviously, this would represent a significant labor and cost savings for manufacturers and would also benefit the consumer by providing for safer foods.

The present invention resolves the aforementioned difficulties in the art while providing other related advantages.

SUMMARY OF THE INVENTION

Within one aspect of the present invention a composition for detecting a target microorganism in a sample is provided which comprises a conditionally detectable marker, wherein the marker is capable of providing a detectable signal when in contact with a viable microorganism, and a substrate for an enzyme that is substantially absent from the target microorganism. In one embodiment the target microorganism is bacteria, yeast, mold, fungi, protozoa, or viruses. In certain embodiments the bacteria is *Salmonella, listeria, E. coli* OH157, *Campylobacter, Staphylococcus aerus, Cryptsporidium*, or *Giardia*.

In the various embodiments, the conditionally detectable marker is detectable by a change in color. In related embodiments, the change in color is produced by the biochemical reduction of tetrazolium red. In yet additional embodiments the substrate comprises a signal moiety linked to the substrate, the signal moiety capable of providing a detectable signal when cleaved by substantially all non-target microorganisms.

In still yet additional embodiments the enzyme is an aminopeptidase, such as an L-alanine-aminopeptidase. In related embodiments the substrate is L-Alanine-7-amido-4-methylcoumarin, L-Alanine-7-amido-4-methylcoumarin TFA, L-Alanine-7-amido-4-trifluoro-methylcoumarin TFA, L-Alanyl-L-alanyl-L-phenylalanine-7-amido-4-methylcoumarin, or L-Alanyl-L-alanyl-L-phenylalanine-7-amido-4-methylcoumarin TFA.

In other embodiments the non-target microorganisms include substantially all non-*Campylobacter* species. While in still additional embodiments the composition further comprises a growth-supporting medium for the target microorganism. In a further embodiment, the growth supporting medium contains all necessary nutrients and growth conditions to properly support the growth of the target microorganism. In still further embodiments the growth supporting medium contains antibiotics to suppress the growth of non-target microorganisms.

In another aspect a medium for detecting viable microorganisms in a sample is provided that comprises a substrate for an aminopeptidase, a conditionally detectable marker, wherein said marker is capable of providing a detectable signal when in contact with a viable microorganism, a signal moiety linked to the substrate, said moiety providing a detectable signal when cleaved by said aminopeptidase from a microorganisms, and a growth supporting medium for target or non-target microorganisms.

In certain embodiments of the medium the aminopeptidase is L-alanine aminopeptidase. While in further embodiments the signal moiety may be ortho-nitrophenyl, 4-methylumbelliferone, para-nitroanilide, 4-methoxy-.beta.-naphthylamide, or 7-amido-4-methylcoumarin. In addition, certain embodiments provide the enzyme substrate selected from N-o-Acetyl-lysine-7-amido-4-methylcoumarin acetate; N-Acetyl-L-phenylalanyl-L-arginine-7-amido-4-methylcoumarin hydrochloride; L-Alanine-7-amido-4-methylcoumarin; β-Alanine-7-amido-4-methylcoumarin TFA; D-Alanine-7-amido-4-methylcoumarin TFA; L-Alanine-7-amido-4-methylcoumarin TFA; L-Alanine-7-amido-4-methylcoumarin TFA; L-Alanine-7-amido-4-trifluoro-methylcoumarin TFA; L-Alanyl-L-alanyl-L-phenylalanine-7-amido-4-methylcoumarin; L-Alanyl-L-alanyl-L-phenylalanine-7-amido-4-methylcoumarin TFA; D-Alanyl-L-leucyl-L-lysine-7-amido-4-methylcoumarin Salt; L-Arginine-7-amido-4-methylcoumarin hydrochloride; L-Arginyl-L-arginine-7-amido-4-methylcoumarin trihydrochloride; L-Asparagine-7-amido-4-methylcoumarin TFA; L-Aspartic acid-b-(7-amido-4-methylcoumarin); N-.alpha.-Benzoyl-DL-arginine-7-amido-4-methylcoumarin; N-.alpha.-Benzoyl-L-arginine-7-amido-4-methylcoumarin; N-Benzoyl-L-phenylalanyl-L-valyl-L-arginine-7-amido-4-methylcoumarin; S-Benzyl-L-cysteine-7-amido-4-methylcoumarin; N-BOC-L-phenylalanyl-L-seryl-L-arginine-7-amido-4-methylcoumarin acetate; N-BOC-L-vanyl-glycyl-L-arginine-7-amido-4-methylcoumarin hydrochloride; N-BOC-L-vanyl-L-leucyl-L-lysine-7-amido-4-methylcoumarin Salt; N-.alpha.-CBZ-L-arginine-7-amido-4-methylcoumarin hydrochloride; N-CBZ-glycylglycyl-L-leucine-7-amido-4-methylcoumarin; N-CBZ-glycyl-L-proline-7-amido-4-methylcoumarin; N-CBZ-glycyl-L-prolyl-L-arginine-7-amido-4-methylcoumarin; N-.beta.-CBZ-L-lysine-7-amido-4-methylcoumarin; N-CBZ-L-phenylalanyl-L-arginine-7-amido-4-methylcoumarin hydrochloride; N-CBZ-L-prolyl-L-arginine-7-amido-4-methylcoumarin hydrochloride; L-Citrulline-7-amido-4-methylcoumarin hydrochloride; L-Citrulline-7-amido-4-methylcoumarin hydrochloride TFA; D-Glutamic acid-.gamma.-(7-amido-4-methylcoumarin); L-Glutamic acid-.alpha.-(7-amido-4-methylcoumarin); L-Glutamine-7-amido-4-methylcoumarin hydrochloride; Glutaryl-glycyl-L-arginine-7-amido-4-methylcoumarin hydrochloride; Glutaryl-glycylglycyl-L-phenylalanine-7-amido-4-methylcoumarin; Glutaryl-L-phenylalanine-7-amido-4-methylcoumarin; Glycine-7-amido-4-methylcoumarin hydrochloride; Glycyl-L-alanine-7-amido-4-methylcoumarin hydrochloride; Glycyl-L-arginine-7- amido-4-methylcoumarin Salt; Glycylglycine-7-amido-4-methylcoumarin hydrochloride; Glycyl-L-phenylalanine-7-amido-4-methylcoumarin; Glycyl-L-proline-7-amido-4-methylcoumarin hydrochloride; L-Histidine-7-amido-4-methylcoumarin; L-Isoleucine-7-amido-4-methylcoumarin; L-Isoleucine-7-amido-4-methylcoumarin TFA; L-Leucine-7-amido-4-methylcoumarin; L-Leucine-7-amido-4-methylcoumarin hydrochloride; L-Leucyl-1-valvyl-1-tyrosine-7-amido-4-methylcoumarin; L-Lysine-7-amido-4-methylcoumarin acetate; L-Methionine-7-amido-4-methylcoumarin acetate; L-Ornithine-7-amido-4-methylcoumarin carbonate; L-Phenylalanine-7-amido-4-methylcoumarin TFA; L-Proline-7-amido-4-methylcoumarin hydrochloride; L-Prolyl-L-phenylalanyl-L-arginine-7-amido-4-methylcoumarin Salt; L-Pyroglutamic acid-7-amido-4-methylcoumarin; L-Serine-7-amido-4-methylcoumarin hydrochloride; L-Seryl-L-tyrosine-7-amido-4-methylcoumarin hydrate; or L-Tyrosine-7-amido-4-methylcoumarin.

In the various embodiments, the linkage between the signal moiety and the substrate is a peptide bond. Further in an additional embodiment, the signal moiety is a fluorescent moiety, and the fluorescent moiety is capable of providing a fluorescent signal or is a chromogen moiety, and the chromogen moiety is capable of providing a signal in the visible, ultraviolet or infrared spectrum.

In still another aspect a method for detecting viable target microorganisms in a sample is provided, comprising providing a medium comprising the aforementioned composition, inoculating the medium with the sample to be tested for the presence of target microorganisms, incubating the inoculated medium under conditions suitable for the growth of target microorganisms wherein the enzyme substrate is capable of being acted upon by an enzyme from substantially all non-target microorganisms to produce a detectable signal, and comparing the difference between the signal generated by conditionally detectable marker and the enzyme substrate, whereby the absence or decrease in a detectable signal indicates the presence of target microorganisms in the sample.

These and other aspects of the present invention will become evident upon reference to the following detailed description. In addition, various references are set forth below which describe in more detail certain procedures or compositions (e.g., dyes, substrates, enzymes, bacteria, yeast, molds, viruses, plasmids, etc.), and are therefore incorporated herein by reference in their entirety.

BRIEF DESCRIPTION OF THE DRAWINGS

FIG. 1 is graph demonstrating the correlative relationship of the inventive methodology compared with standard Campy-Cefex Agar counting of *Campylobacter*. The comparison was performed with 162 poultry wash samples subjected to the inventive assay as compared to the results achieved for the same samples using the industry and USDA accepted Campy-Cefex Agar test.

DETAILED DESCRIPTION OF THE INVENTION

Prior to setting forth the invention, it may be helpful to an understanding thereof to set forth definitions of certain terms that will be used hereinafter.

As used herein a "conditionally detectable marker" refers to a molecule that undergoes a measurable change (such as a color change) when reacted upon by a viable microorganism in a sample. Thus the condition in "conditionally detectable" refers to the condition of viability. Such molecules are commonly referred to as Vital Dyes within the art, to denote a dye or marker which is acted upon substantially only by viable cells, such as red-ox dyes (resazurin, XTT, MTT etc.). A listing of such dyes is available in the art (see, e.g., Sigma Chemical catalog 2000-2001, page 1836, 2000, St. Louis, Mo. or Molecular Probes catalog 2000-2001, Eugene, Oreg.). In one embodiment, the biochemical activity of a dye is used to detect or measure the concentration of a microorganism in a sample. In another embodiment, the specific dye is tetrazolium-red; as disclosed herein, this dye has been shown to be reduced by *Campylobacter* species and is well known by those in the art to reduced by most microorganisms. Vital dye..any dye that can be used to determine viability.

As used herein an "enzyme substrate" refers to a molecule on which an enzyme acts. The enzymatic reaction usually involves hydrolyzing one or more covalent bonds. In one aspect the substrate comprises linked nutrient and detectable moieties. By being hydrolyzed by a microbial enzyme, the substrate liberates a separate detectable moiety in the medium. In another aspect, the enzymatic product of a natural substance is detectable with a separate detectable moiety. In preferred embodiments, the enzyme substrate is selected from the group of substrates listed in Table III. This list is not meant to exclude any enzyme substrate which have yet to be discovered, substrates which may later be identified and included in this list by those of ordinary skill in the art. In certain embodiments, the enzyme substrate is L-alanine 7-amido-4-methylcoumarin.

As used herein a "medium" refers to an environment, typically liquid or solid, in or upon which microorganisms can grow and reproduce. It is an environment which is constructed by those skilled in the art to provide for detectable growth of the target microorganism. Composition of the medium can vary depending upon the nature of the target microorganism but, in general, will contain effective concentrations of components which include by not necessarily limited to: amino acids, vitamins, carbohydrates, a nitrogen source, lipids, fatty acids, minerals, trace elements, and antimicrobial agents.

As used herein "nutrient moiety" refers to a molecule or substance which is a nutrient or metabolic source for at least the non-target microorganisms, including but not limited to :amino acids (e.g., alanine, leucine, arginine, valine, etc. . . . ), carbon sources (e.g., D-glucose, D-fructose, D-lactose, etc. . . . ), minerals (e.g., sulfate, phosphate, calcium, etc. . . . ). In one preferred embodiment of the invention, the nutrient moiety of the enzyme substrate is an amino acid.

As used herein "detectable moiety" refers to a molecule or substance which can be affiliated with a nutrient moiety or exist as a discrete entity. The detectable moiety does not cause or produce a detectable signal when it is affiliated with (e.g., covalently bonded to) a nutrient moiety. However, when an enzyme from a microorganism hydrolyzes the substrate, a detectable moiety is released and causes or is capable of producing a detectable signal. In preferred embodiments, the detectable moiety is a chromogen which preferably produces a color change in the visible wavelength range (alternatively in the ultraviolet or infrared spectra), or fluorogens which emit fluorescence when properly excited by an external energy source. Examples of detectable moieties include, but are not limited to: ortho-nitropenyl, 4-methylumbelliferone, para-nitroanilide, 4-methoxy-β-naphthylamide, 7-amido-4-methylcoumarin.

As used herein a "detectable signal" refers to a characteristic change in a medium or sample that is observable or measurable by physical, chemical, or biological means known to those skilled in the art. Such a detectable signal may be assayed by visual, tactile, or olfactory means. For example, a change in emission or absorbance of visible or invisible light or radio waves at a certain wavelength, electrical conductivity, emission of gas, or odor is detected. A detectable signal may also be a change in the physical state such as between solid, liquid, and gas. Typically, a detectable signal is measured visually; in preferred embodiments, detectable signals comprise a change in color or fluorescent emission of the medium.

As used herein a "sample" refers to a component taken from a food product, a human or animal test sample, pharmaceutical or cosmetic commodity, soil, water, air or other environmental source, or any other source from which a target organism is to be detected. A test sample may be taken from a source using techniques known to those skilled in the art. In preferred embodiments, the test sample is a poultry rinse water sample.

As used herein a "target microorganism" refers to any viable unicellular microorganism the detection of which is required to determine the quality, safety, or other specification of a particular test sample. These target microorganisms include but are not necessary limited to bacteria, yeast, mold, fungi, parasites, and viruses. In preferred embodiments the target microorganisms are *Campylobacter* species.

As used herein "non-target microorganism" refers to substantially all viable unicellular microorganisms capable of growth and detection in the medium that are not the target microorganism.

As used herein "effective concentrations of components" refers to an amount of nutrients or antimicrobial agents within the range which allows or promotes growth and reproduction of the target microorganism. That is, an amount which allows the target microorganism to adapt to the medium, continue metabolism, or synthesize the necessary constituents for reproduction and to subsequently reproduce.

As used herein the terms "amino acids", "vitamins", "carbohydrates", "a nitrogen source", "lipids", "fatty acids", "minerals", "trace elements", and "antimicrobial agents" refer to include all molecules, compounds, and substances classified in each category by those of skill in the art whether organic or inorganic. The combination of these categories is intended to include any substance which may be necessary for, or conducive to, maintaining life of the target microorganism.

As used herein the term "presumptive detection of target microorganisms" refers to the fact that the medium allows sensitive (i.e., at least 50%) detection of the target microorganism, as measured relative to a generally accepted standard culture procedure.

As used herein the term "substantially" refers to at least 90, 91, 92, 93, 94, 95, 96, 97, 98, 99 and 100% of the particular microorganism capable of growing and reproducing in the medium.

The term "effective amount of nutrients" is an amount of nutrients within the range which allows or promotes growth and reproduction of a target microorganism. That is, an amount which allows target microbes or other organisms to adapt to the medium; continue metabolism; or, synthesize the necessary constituents for reproduction and to subsequently reproduce.

The term "medium" means a solid, powder or liquid mixture which contains all or substantially all of the nutrients necessary to allow a microbe to grow and reproduce. This invention includes both media which are sterilized as well as media which are not sterile.

The term "target microorganism" refers to a microorganism whose presence or absence is sought to be detected.

The term "aminopeptidase" refers to an enzyme whose enzymatic activity is capable of hydrolyzing a covalently linked peptide bond of an enzyme substrate or a plurality of enzyme substrates. In a preferred embodiment of this invention, the enzymatic activity of one or more aminopeptidases is used to detect or measure the concentration of yeasts and molds in a sample. In one preferred embodiment, the aminopeptidase enzyme is alanine aminopeptidase.

The term "liquefied" as used herein refers to a state of matter substantially in liquid form, though it is also meant to include pulverized or homogenized samples of solid substances having at least a 10% liquid content. Liquefied medium is distinct from a gelled medium, such as is found with agar-based medium.

"Bacteria" as used herein is meant to encompass the term as used within the art, including all bacterial forms (See, Bergeys Manual of Systematic Bacteriology, Lippincott, Williams, and Wilkins, 1989).

The term "yeast" as used herein refers to a typically unicellular fungus that reproduces asexually. Yeast includes one or more species of the following organisms existing or co-existing collectively in a test sample. For example, yeasts include those listed in Table I and described in: Tibor Deak and Larry Beuchat, Handbook of Food Spoilage Yeasts, pp. 3-11, 124-25 (1996) and James, M. Jay, Modem Food Microbiology, 4th Ed., pp. 26-35 (1992) each of which are incorporated by reference herein. The term "yeasts" also refers to the array of yeasts found, e.g., in a test sample. The term is not limited to mean any given number of these species and is not meant to exclude species which have yet to be discovered but may later be identified and included in this definition by those of skill in the art.

TABLE I

Common Foodborne Yeast Genera 60 Common Yeast Strains (93% Combined Frequency in Foods)
Genera Top 60 Foodborne Yeast Strains

*Candida Candida boidinii Kluyveromyces marxaanus*
*Cryptococcus Candida apicola Metschnikowia pulcherrima*
*Debaryomyces Candida albicans Pichia angusta*
*Galactomyces Candida zeylanoides Pichia subpelliculosa*
*Hanseniaspora Candida vini Pichia mambranaefaciens*
*Issatchenkia Candida versatilia Pichia jadinii*
*Kluyveromyces Candida tropicalis Pichia guilliermondii*
*Metschnikowia Candida stellata Pichia fermentans*
*Pichia Candida sake Pichia farinosa*
*Rhodotorula Candida rugosa Pichia burtonii*
*Saccharomyces Candida parapsilosis Pichia anomala*
*Saccharomycodes Candida norvergica Rhodotorula glutinis*
*Schizosaccharomyces Candida magnoliae Rhodotorula mucilaginosa*
*Sporobolmyces Candida intermedia Rhodotorula minuta*
*Torulaspora Candida incospicua Saccharomyces bayanus*
*Trichosporon Candida glabrata Saccharomyces kluyveri*
*Yarrowia lipolytica Candida etchellsii Saccharomyces exiguus*
*Zygosacchromyces Candida catenulata Saccharomyces cerevisiae*
*Cryptococcus albidus Saccharomycodes ludwigii*
*Cryptococcus laurentii Saccharomycopsis fibuligera*
*Cryptococcus humicolus Saccharomycopsis pombe*
*Debaryomyces etchellsii Sporobolmyces roseus*
*Debaryomyces polymorphus Torulaspora delbrueckii*
*Debaryomyces hansenii Trichosporon moniliforme*
*Galactomyces geotrichum Trichosporon pullulans*
*Haneniaspora guilliermonii Yarrowia lipolytica*
*Haneniaspora uvarum Zygosacchromyces bailii*
*Issatchenkia orientalis Zygosacchromyces rouxii*
*Kluyveromyces lactis Zygosacchromyces microellipsoides*
*Kluyveromyces thermotolerans Zygosacchromyces bisporus*

The term "mold" as used herein refers to a fungus. For example, mold includes one or more species of the following microorganisms existing or co-existing collectively in a test sample: Aspergillus, Penicillin etc. This term is not limited to mean any given number of these species and is not meant to exclude species which have yet to be discovered but may later be identified and included in this genus by those skill in the art. The molds include those listed in Table II and described or referred to Modern Food Microbiology, 4th Ed., supra.

TABLE II

Common Foodborne Mold Genera
Genera Important Foodborne Mold Strains

Alternaria Alternaria citri Fusarium graminearum
Aspergillus Alternaria alternata Fusarium tricinctum
Botrytis Alternaria solani Geotrichum candidum
Byssochlamys Alternaria tenuissima Geotrichum albidum
Cladosporium Aspergillus niger Monilia sitophila
Colletotrichum Aspergillus alliaceus Mucor miehei
Fusarium Aspergillus ostianus Penicillium roqueforti
Geotrichum Aspergillus mellus Penicillium cyclopium
Monilia Aspergillus clavatus Penicillium patulum
Mucor Aspergillus terreus Penicillium expansum
Penicillium Aspergillus soyae Penicillium clavifome
Pullularia Aspergillus glaucus Penicillium viridicatum
Rhizopus Aspergillus oryzae Penicillium citrinum
Thamnidium Aspergillus parasiticus Pullularia pullulans
Trichothecium Botrytis cinerea Rhizopus stolonifer
Byssochlamys fluva Rhizopus oligosporus
Byssochlamys nivea Thamnidium elegans
Cladosporium herbarum Trichothecium roseum
Cladosporium Colletotrichum
cladosporiodes gloeosporioides In the various embodiments, microbial aminopeptidases include, but are not limited to alanine aminopeptidase. In certain embodiments, the peptidase substrates are selected from the group of aminopeptidase fluorogenic substrates that are listed in Table III. It is to be understood that this list does not exclude other known enzymatic substrates, including chromogenic aminopeptidase substrates (e.g., p-nitroanline tagged species), and aminopeptidase substrates which have yet to be discovered but later identified and included in this list by those of ordinary skill in the art.

TABLE III

AMC (7-Amido-4-methylcoumarin) Aminopeptidase Substrates

N-o-Acetyl-lysine-7-amido-4-methylcoumarin acetate
N-Acetyl-L-phenylalanyl-L-arginine-7-amido-4-methylcoumarin hydrochloride
L-Alanine-7-amido-4-methylcoumarin
.beta.-Alanine-7-amido-4-methylcoumarin TFA
D-Alanine-7-amido-4-methylcoumarin TFA
L-Alanine-7-amido-4-methylcoumarin TFA
L-Alanine-7-amido-4-methylcoumarin TFA
L-Alanine-7-amido-4-trifluoro-methylcoumarin TFA
L-Alanyl-L-alanyl-L-phenylalanine-7-amido-4-methylcoumarin
L-Alanyl-L-alanyl-L-phenylalanine-7-amido-4-methylcoumarin TFA
D-Alanyl-L-leucyl-L-lysine-7-amido-4-methylcoumarin Salt
L-Arginine-7-amido-4-methylcoumarin hydrochloride
L-Arginyl-L-arginine-7-amido-4-methylcoumarin trihydrochloride
L-Asparagine-7-amido-4-methylcoumarin TFA
L-Aspartic acid-.beta.-(7-amido-4-methylcoumarin)
N-.alpha.-Benzoyl-DL-arginine-7-amido-4-methylcoumarin
N-.alpha.-Benzoyl-L-arginine-7-amido-4-methylcoumarin
N-Benzoyl-L-phenylalanyl-L-valyl-L-arginine-7-amido-4-methylcoumarin
S-Benzyl-L-cysteine-7-amido-4-methylcoumarin
N-BOC-L-phenylalanyl-L-seryl-L-arginine-7-amido-4-methylcoumarin acetate
N-BOC-L-vanyl-glycyl-L-arginine-7-amido-4-methylcoumarin hydrochloride
N-BOC-L-vanyl-L-leucyl-L-lysine-7-amido-4-methylcoumarin Salt
N-.alpha.-CBZ-L-arginine-7-amido-4-methylcoumarin hydrochloride
N-CBZ-glycylglycyl-L-leucine-7-amido-4-methylcoumarin
N-CBZ-glycyl-L-proline-7-amido-4-methylcoumarin TABLE III-continued AMC (7-Amido-4-methylcoumarin) Aminopeptidase Substrates N-CBZ-glycyl-L-prolyl-L-arginine-7-amido-4-methylcoumarin
N-.beta.-CBZ-L-lysine-7-amido-4-methylcoumarin
N-CBZ-L-phenylalanyl-L-arginine-7-amido-4-methylcoumarin hydrochloride
N-CBZ-L-prolyl-L-arginine-7-amido-4-methylcoumarin hydrochloride
L-Citrulline-7-amido-4-methylcoumarin hydrochloride
L-Citrulline-7-amido-4-methylcoumarin hydrochloride TFA
D-Glutamic acid-.gamma.-(7-amido-4-methylcoumarin)
L-Glutamic acid-.alpha.-(7-amido-4-methylcoumarin)
L-Glutamine-7-amido-4-methylcoumarin hydrochloride
Glutaryl-glycyl-L-arginine-7-amido-4-methylcoumarin hydrochloride
Glutaryl-glycylglycyl-L-phenylalanine-7-amido-4-methylcoumarin
Glutaryl-L-phenylalanine-7-amido-4-methylcoumarin
Glycine-7-amido-4-methylcoumarin hydrochloride
Glycyl-L-alanine-7-amido-4-methylcoumarin hydrochloride
Glycyl-L-arginine-7-amido-4-methylcoumarin Salt
Glycylglycine-7-amido-4-methylcoumarin hydrochloride
Glycyl-L-phenylalanine-7-amido-4-methylcoumarin
Glycyl-L-proline-7-amido-4-methylcoumarin hydrochloride
L-Histidine-7-amido-4-methylcoumarin
L-Isoleucine-7-amido-4-methylcoumarin
L-Isoleucine-7-amido-4-methylcoumarin TFA
L-Leucine-7-amido-4-methylcoumarin
L-Leucine-7-amido-4-methylcoumarin hydrochloride
L-Leucyl-1-valvyl-1-tyrosine-7-amido-4-methylcoumarin
L-Lysine-7-amido-4-methylcoumarin acetate
L-Methionine-7-amido-4-methylcoumarin acetate
L-Ornithine-7-amido-4-methylcoumarin carbonate
L-Phenylalanine-7-amido-4-methylcoumarin TFA
L-Proline-7-amido-4-methylcoumarin hydrochloride
L-Prolyl-L-phenylalanyl-L-arginine-7-amido-4-methylcoumarin Salt
L-Pyroglutamic acid-7-amido-4-methylcoumarin
L-Serine-7-amido-4-methylcoumarin hydrochloride
L-Seryl-L-tyrosine-7-amido-4-methylcoumarin hydrate
L-Tyrosine-7-amido-4-methylcoumarin In one aspect, this invention provides a medium for the detection of a target microorganism in a sample. In a preferred embodiment the medium comprises: an enzyme substrate (e.g., an aminopeptidase); a conditionally detectable marker; and a growth supporting medium.

Prior to this invention, microbiologists employed one of two strategies to enhance the specificity of the microbial diagnostic test being developed. The most popular method is the use of antimicrobial agents to suppress the growth and detection of non-target microorganisms. The second, much less popular method, is the use of a specific, highly selective, indicator for the target microorganism itself. Unfortunately, this strategy has a very limited applicability because, in practice, it is very difficult to find such a indicator for each microorganism being detected. With the invention disclosed herein, a much more widely applicable approach is revealed which utilizes a presumptive indicator for the target microorganism and non-target microorganisms capable of growth and detection in the medium followed by a confirmation indicator, which is substantially only reacted upon by the non-target microorganisms. Such a strategy has broad applicability. As mentioned above, due to the immediate need in the art, the bacteria Campylobacter is used herein as the prototypical example. However, one of ordinary skill in the art would readily conclude that the general scheme can be extended to all microorganisms.

The enzyme L-alanine aminopeptidase was thought to be ubiquitous among gram negative bacteria. Previous work had even suggested that measuring the activity of this enzyme by incorporating an appropriate enzyme substrate directly into a bacterial growth medium could be used to specifically detect and quantify the concentration of gram negative bacteria in a sample. Surprisingly, Campylobacter species do not express this enzyme activity in standard biochemical assays. The present invention comprises that presumptive detection of a target microorganisms (for example, *Campylobacter* species) can be achieved colorimetrically in a suitable medium containing a conditionally detectable marker (for example, the dye tetrazolium-red) and their identity confirmed by the absence of an enzymatic activity (for example, L-alanine aminopeptidase) known to be present in substantially all non-target microorganisms.

Accordingly, a medium is disclosed for detecting target microorganisms specifically exemplifying the detection of *Campylobacter* species in a test sample. In certain preferred embodiments, the medium provides an effective result by employing a conditionally detectable marker for presumptive detection of *Campylobacter* species and a detectable enzyme substrate for an enzyme not expressed in *Campylobacter* species the absence of which confirms the presence of *Campylobacter* species. In addition, buffer ingredients, carbohydrates, amino acids, trace elements, salts, and growth stimulators are provided in the medium to allow sufficient growth of these target organisms, so that the detectable signals in the sample due to the biochemical reduction of tetrazolium-red by the *Campylobacter* species and the hydrolysis of the L-alanine aminopeptidase substrate by the non-*Campylobacter* species is more effectively observed. In further preferred embodiments, antimicrobial agents are added to the medium to suppress the growth of certain non-*Campylobacter* species, for example, polymixin B. vancomycin, cycloheximide, rifampicin, amphotericin B (for yeast and mold), cephaperazone, and the like as appropriate.

With respect to the prototypical sample, *Campylobacter*, this species has been shown to biochemically reduce the dye tetrazolium-red resulting in the production of an intense red color. Campy Line agar was developed by the USDA as an agar based *Campylobacter* selection agar and contains tetrazolium-red to stain *Campylobacter* and non-*Campylobacter* colonies red after a 48 hour incubation period. The suppression of non-target (i.e., non-*Campylobacter*) bacteria on this agar is achieved solely by the use of antibiotics which are incorporated into the medium during production. See, e.g., Janet E. L. Corry, *International Journal of Food Microbiology* 26:43-76, 1995. Suppression of the non-target organisms is not very accurate, therefore, supplemental reactions are still required to confirm the presence of *Campylobacter* species on this medium. In fact, as with many detection methods for microorganisms, all existing methods for the detection of *Campylobacter* have an absolute requirement for the presence of antibiotics in the growth medium to suppress non-target growth and complicated supplemental reactions to confirm the identity of presumptive *Campylobacter* colonies.

One way to avoid the complicated confirmation steps is to discover a way in which to distinguish *Campylobacter* species from non-*Campylobacter* organisms directly in the growth medium (e.g., colorimetrically). To do this, one would need to incorporate an enzyme substrate containing a detectable moiety into the growth medium that the *Campylobacter* species can not hydrolyze but substantially all the non-*Campylobacter* organisms can. One exemplary example is the enzyme substrate, L-alanine-7-amido-4-methylcoumarin which is hydrolyzed by the enzyme L-alanine aminopeptidase, fulfills this role.

With this invention, the problems and issues encountered with the development of microbial diagnostic tests have been significantly reduced. This is accomplished by incorporating a detection scheme directly in the growth medium containing presumptive positive and confirmed positive indicators for a target microorganism. The presumptive indicator is reacted upon by the target microorganism and any non-target microorganisms capable of growth in the medium resulting in the production of a measurable signal. The confirmed indicator is reacted upon substantially only by the non-target microorganisms resulting in a different detectable signal. The absence of a signal from this indicator is indicative of the presence of the target microorganism. A example of such a detection scheme that has been put into practice is described below for the detection of *Campylobacter* species in poultry rinse water samples. However, this invention can be extended to any such microorganism, wherein the target microorganism has substantially less of a particular enzyme as opposed to the non-target organisms likely to present in the sample.

For the first time in the art, the presence of a target microorganism in a sample can be detected with a high degree of sensitivity and selectivity by combining presumptive and confirmation steps directly in the growth medium without the need for transfer steps, supplemental tests, a cocktail of antimicrobial agents, or use of nutrient indicators. In this invention the presumptive test is a generalized indicator which can be biochemically altered by substantially all the microorganisms capable of growth in the medium and the confirmation test is the absence of some unique metabolic activity in the target microorganism which is present in the non-target microorganisms. This approach has been put into practice for the detection of *Campylobacter* species in a sample by their ability to reduce the dye tetrazolium-red and their inability to hydrolyze the aminopeptidase substrate L-alanine-7-amido-4-methylcoumarin. As disclosed herein, these chemicals can be incorporated into a suitable growth medium, the development of which is well known to those skilled in the art.

The ability of *Campylobacter* species to biochemically reduce tetrazolium-red into a red colored molecule has been well documented. However, until the unexpected discovery that *Campylobacter* species lack the ability to express L-alanine aminopeptidase activity, it was not possible to confirm that these red color producing microorganisms where in fact *Campylobacter* unless a series of complicated confirmation steps were carried out. It was unexpected that *Campylobacter* species would lack the ability to express this enzyme activity because the art teaches that L-alanine aminopeptidase activity is ubiquitous among gram negative rod shaped bacteria, and thus, would be expected to be present in *Campylobacter* species. Therefore, similar lack of function analysis for other microbial detection systems where application of this presumptive/confirmation enzymatic screen can be applied.

Thus, various aspects of the present invention feature a composition medium for the presumptive detection of *Campylobacter* species by their ability to react to a conditionally detectable marker; in one embodiment the marker is the dye tetrazolium-red, the identity of these organisms being confirmed by the absence of an enzyme activity; in one embodiment the enzyme is L-alanine aminopeptidase. Presumptive detection of *Campylobacter* species is achieved by the appearance of a red color in the medium which is confirmed by the absence of fluorescence.

In a preferred embodiment, at least one conditionally detectable marker is included in a growth medium capable of reacting with *Campylobacter* species along with at least one enzyme substrate hydrolyzed by an enzyme not found in *Campylobacter* species but common among non-*Campylobacter* species capable of growth and reproduction in the medium. In preferred embodiments, the signal produced by the conditionally detectable marker and the hydrolyzed enzyme substrate are different. In certain embodiments, the conditionally detectable marker is tetrazolium-red. In further embodiments, the enzyme substrate is L-alanine-7-amido-4- methylcoumarin. In preferred embodiments, the medium contains an effective amount of biological buffers, carbohydrates, vitamins, amino acids, elements, salts, growth stimulators, and selective agents to provide viability and specific enrichment of *Campylobacter* species in the presence of tetrazolium-red and L-alanine-7-amido-4-methylcoumarin. In addition, although the presently preferred L-alanine aminopeptidase substrate is L-alanine-7-amido-4-methylcoumarin, it is to be understood that this does not exclude other known chromogenic, flourogenic or otherwise detectable substrates for this enzyme and substrates which have yet to be discovered but later identified by those of ordinary skill in the art as being suitable alternatives to this substrate.

The invention also provides a method to detect *Campylobacter* species in a test sample. The medium is inoculated with the test sample and incubated under conditions suitable for the growth of *Campylobacter* species for a certain period of time, preferably between 12 to 60 hours, and more preferably between 18 to 52 hours, including every integer in the range of numbers between 12 to 60 and 18 to 52 hours. The production, e.g., biochemically reduced tetrazolium red and the absence of fluorescence from hydrolyzed L-alanine-7-amido-4-methylcoumarin, indicates the presence of confirmed *Campylobacter* species in the test sample.

In a preferred embodiment, the medium is comprised in a powder form. The powder is preferably liquefied with sterile dilutent before a test sample is inoculated with the medium. The incubation may be performed microaerophillically at 42° C.

In another preferred embodiment, the method uses a gelled medium. A preferred medium is an agar medium that comprises tetrazolium (or related compound) and L-alanine-7-amido-4-methylcoumarin (or related substrate).

In yet another aspect, the invention provides a method for quantifying the number of *Campylobacter* species in a test sample. In this aspect, the invention is a method to enumerate the amount of *Campylobacter* species in a sample by contacting the sample with the subject medium, placing the sample and medium mixture in containers, incubating the sample and medium mixture, observing the quantity and quality of detectable characteristic signals, and comparing the quantity of detectable characteristic signals with most probable number values. This quantifying process comprises comparing the quantity and quality of the characteristic which has been altered, preferably a color change and/or even a fluorescent change, to statistically determine the most probably number of *Campylobacter* species in the test sample. Such statistical determinations take place in accordance with the methodologies known to those in the art. The most probable number (MPN) technique is based on probability statistics. The results from any type of an MPN analysis are directly related to the frequency of occurrence of a series of positive results that are most likely to occur when certain numbers of organisms are present in a test sample.

The composition of the invention is preferably added to medium which is preferably used to conduct assays in multiwell microtiter plates. In preferred embodiments, the invention is used with the apparatus described by Croteau et al. in U.S. Pat. No. 5,985,594 or that described by Croteau et. al. in U.S. Pat. No. 5,700,655, each of which are hereby incorporated by reference; assay devices incorporating such technology are marketed under the tradename SimPlate® (BioControl Systems, Inc., Bellevue, Wash.). The quantifying step preferably involves providing a sample of an environmental or biological sample into a liquefied medium of the invention, placing or dispensing the mixture of sample and medium into a device described by Croteau et. al., incubating the sample, detecting the quantity and quality of the detection moiety characteristic, and optionally comparing the quantity of the characteristic signal with the most probable number values. Preferably, the incubation step is carried out at 42° C. for a period of 48 to 52 hours in a microaerophillic incubator using the medium described above or other favorable temperature and time as is appropriate for the particular microorganism.

Using the medium and methods of this invention, the *Campylobacter* concentration in a test sample can be determined much more easily and quickly than by methods currently available.

In the various embodiments the number of target microbes present in a liquid sample may be quantified by mixing a liquid sample with the medium described above, placing the liquid sample including the medium in suitable containers for incubation, incubating the liquid sample and medium mixture, observing the quantity and quality of a detectable characteristic signal, and comparing the quantity and quality of a detectable characteristic signal with most probable number values. This quantifying process features comparing the quantity and quality of the characteristic which has been altered, preferably a color change, to most probable number values obtained from samples where the concentration and characteristic change have been correlated with samples for which bacterial concentration is known. See e.g., Compendium of Methods for the Microbiological Examination of Foods 3rd ed., Edited by Vanderzant and Splittstoesser, 1992. The most probable number technique allows estimates of bacterial concentrations that are below detectable limits of other methods. The most probable number is estimated from responses where the results are reported as positive or negative in one or more dilutions of the sample. The method requires that not all samples provide a positive result and usually at least three samples of each dilution are required. Many most probable number charts are available. One such series is provided by de Man, *Eur. J. Appl. Microbiol.* 1:67 (1975) herein incorporated by reference. Estimates of the most probable number may be made using the general formula reported by Thomas, *J. Am. Water Works Assoc.* 34:572 (1942) as follows:

$$MPN/g = P/(NT)$$

where P is the number of positive tubes, N is the total quantity of sample in all negative tubes, and T is the total quantity of sample in all tubes. The quantities are reported in terms of grams.

EXAMPLES

Example I

Detection of *Campylobacter* in Poultry Wash Samples

A total of twenty poultry rinse water samples were collected from a Canadian poultry plant. One ml aliquots of each rinse water sample were added to 9 ml samples of a medium containing the dye tetrazolium-red and the aminopeptidase substrate L-alanine-7-amido-4-methylcoumarin. Each 10 ml mixture was transferred to SimPlate devices also sold by BioControl Systems, Inc. and placed in a 42° C. microaerophillic (5% $O_2$ and 10% $CO_2$) incubator. One ml aliquots of each rinse water sample were also streaked onto 4 Campy Line agar plates (0.25 ml per plate). These plates were also placed in a 42° C. microaerophillic incubator. All tests were incubated for 48 hours.

The SimPlates were removed from the incubator after 48 hours and the number of red wells (presumptive positive for *Campylobacter*) were counted for each plate. Next, a portable (366 nm) UV light was illuminated over each red well to check for fluorescence. The absence of fluorescence in each presumptive positive well was considered confirmed positive for *Campylobacter*. The number of confirmed positive wells for each plate converted into the number of organisms per ml of rinse water sample by using the Conversion Table provided by the manufacturer.

The Campy Line agar plates were removed from the incubator after 48 hours and the number of red colonies were counted for each rinse water set of plates. Suspecter *Campylobacter* colonies were streaked onto AHB plates and incubated overnight in a 42° C. microaerophillic incubator. Isolates which grew on the AHB plates were subjected to immunoprecipitation reactions to confirm the presence of *Campylobacter* species. Confirmed *Campylobacter* isolates were enumerated for each set of plates and expressed as the number of colony forming units (CFU) per ml of rinse water sample. The results of this study are shown below:

| Sample | SimPlate (organisms/ml) | Line agar (CFU/ml) |
|---|---|---|
| 1 | 80 | 104 |
| 2 | 414 | 302 |
| 3 | 392 | 381 |
| 4 | 288 | 227 |
| 5 | 50 | 67 |
| 6 | 56 | 82 |
| 7 | 124 | 120 |
| 8 | 440 | 367 |
| 9 | 86 | 79 |
| 10 | 40 | 46 |
| 11 | 100 | 111 |
| 12 | 86 | 76 |
| 13 | 624 | 673 |
| 14 | 112 | 78 |
| 15 | 132 | 207 |
| 16 | 116 | 126 |
| 17 | 84 | 79 |
| 18 | 184 | 145 |
| 19 | 68 | 87 |
| 20 | 104 | 110 |

Example II

Correlation of Campy-Cefex Agar Detection of *Campylobacter* in Poultry Wash Samples with Inventive Method Assays were performed as above, except instead of Campy-Line Agar plates, Campy-Cefex agar plates were utilized 162 poultry washes performed as above were compared. The Campy-Cefex agar assay was performed as described by in United States Department of Agriculture ARS, Poultry Microbiological Safety Research Unit, Method for the Enumeration of *Campylobacter* species from Poultry Rinses, Mar. 15, 2000, and confirmed positive for *Campylobacter* by subsequent agglutination assays. The results of this comparison are depicted in FIG. 1. As can be appreciated from reviewing the FIGURE, the data were highly correlative and demonstrate the usefulness of the inventive assay to attain similar results in much quicker time without the laborious steps required by the standard methods.

From the foregoing it will be appreciated that, although specific embodiments of the invention have been described herein for purposes of illustration, various modifications may be made without deviating from the spirit and scope of the invention. Further, all of the references, including publications, journal articles, patents, and patent applications, herein mentioned are hereby incorporated by reference in their entirety. Accordingly, the invention is not limited except as by the appended claims.

The invention claimed is:

1. A composition for detecting a target microorganism in a sample, comprising a growth-supporting medium for the specific enrichment of a target microorganism, wherein said growth-supporting medium contains antibiotics to suppress the growth of non-target microorganisms and a conditionally detectable marker that undergoes a color change when reacted upon by a viable microorganism in the sample, wherein the color change is produced by a biochemical reduction of the conditionally detectable marker, and a substrate for an aminopeptidase, wherein said aminopeptidase is substantially absent from the target microorganism, wherein said target microorganism is *Campylobacter*, wherein said substrate comprises a signal moiety, the signal moiety capable of providing a detectable signal when cleaved by non-target microorganisms in the sample, and wherein said conditionally detectable marker and said substrate for an aminopeptidase are not the same molecule.

2. The composition of claim 1, wherein said conditionally detectable marker comprises tetrazolium red.

3. The composition of claim 1, wherein said growth supporting medium contains all necessary nutrients and growth conditions to properly support the growth of the target microorganism.

4. A composition for detecting *Campylobacter* in a sample, comprising a growth-supporting medium for the specific enrichment of *Campylobacter*, wherein said growth-supporting medium contains antibiotics to suppress the growth of non-target microorganisms and a conditionally detectable marker that undergoes a color change when reacted upon by a viable microorganism in the sample, and a substrate for an L-alanine-aminopeptidase, wherein said aminopeptidase is substantially absent from the *Campylobacter* target microorganism, wherein said substrate comprises a signal moiety, the signal moiety capable of providing a detectable signal when cleaved by non-target microorganisms in the sample, and wherein said conditionally detectable marker and said substrate for said aminopeptidase are not the same molecule.

5. The composition of claim 4, wherein said substrate is selected from the group consisting of L-Alanine-7-amido-4-methylcoumarin, L-Alanine-7-amido-4-methylcoumarin TFA, L-Alanine-7-amido-4-trifluoro-methylcoumarin TFA, L-Alanyl-L-alanyl-L-phenylalanine-7-amido-4-methylcoumarin, and L-Alanyl-L-alanyl-L-phenylalanine-7-amido-4-methylcoumarin TFA.

6. The composition of claim 5, wherein said substrate is L-alanine-7-amido-4-methylcoumarin.

* * * * *